(12) United States Patent
Pianca

(10) Patent No.: US 9,295,830 B2
(45) Date of Patent: *Mar. 29, 2016

(54) METHODS FOR MAKING LEADS WITH SEGMENTED ELECTRODES FOR ELECTRICAL STIMULATION SYSTEMS

(71) Applicant: BOSTON SCIENTIFIC NEUROMODULATION CORPORATION, Valencia, CA (US)

(72) Inventor: Anne Margaret Pianca, Santa Monica, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/481,749

(22) Filed: Sep. 9, 2014

(65) Prior Publication Data

US 2014/0379061 A1    Dec. 25, 2014

Related U.S. Application Data

(63) Continuation of application No. 13/275,112, filed on Oct. 17, 2011, now Pat. No. 8,862,242.

(60) Provisional application No. 61/426,784, filed on Dec. 23, 2010.

(51) Int. Cl.
*A61N 1/375*    (2006.01)
*A61N 1/05*    (2006.01)

(52) U.S. Cl.
CPC ............ *A61N 1/0529* (2013.01); *A61N 1/0551* (2013.01); *Y10T 29/49117* (2015.01); *Y10T 29/49208* (2015.01); *Y10T 29/53204* (2015.01); *Y10T 29/53209* (2015.01)

(58) Field of Classification Search
CPC ........................... A61N 1/0529; A61N 1/0551
See application file for complete search history.

(56) References Cited

U.S. PATENT DOCUMENTS 4,602,624 A    7/1986 Naples et al.
4,630,611 A    12/1986 King
(Continued)

FOREIGN PATENT DOCUMENTS

EP    0580928 A1    2/1994
EP    0650694 B1    7/1998
(Continued)

OTHER PUBLICATIONS

U.S. Appl. No. 14/557,211, filed Dec. 1, 2014.
U.S. Appl. No. 14/286,940, filed May 23, 2014.
U.S. Appl. No. 14/286,889, filed May 23, 2014.
U.S. Appl. No. 14/286,829, filed May 23, 2014.
U.S. Appl. No. 14/325,249, filed Jul. 7, 2014.
(Continued)

*Primary Examiner* — Joseph Dietrich
(74) *Attorney, Agent, or Firm* — Lowe Graham Jones PLLC; Bruce E. Black

(57) ABSTRACT

One embodiment is a method of making a stimulation lead that includes providing a pre-electrode assembly comprising a plurality of segmented electrodes and a plurality of raised connectors. Each of the segmented electrodes is coupled to at least one other of the segmented electrodes by at least one of the raised connectors. The method further includes forming the pre-electrode assembly into a tube with the tube defining a longitudinal axis. Each of the raised connectors is disposed at a radius with respect to the longitudinal axis that is greater than a radius of any of the segmented electrodes with respect to the longitudinal axis. The method also includes forming at least a portion of a lead body around the segmented electrodes of the pre-electrode assembly; and grinding the tube comprising the pre-electrode assembly and portion of the lead body to remove the plurality of raised connectors leaving the plurality of segmented electrodes and the portion of the lead body.

20 Claims, 7 Drawing Sheets

(56) References Cited

U.S. PATENT DOCUMENTS

| | | |
|---|---|---|
| 4,744,370 A | 5/1988 | Harris |
| 5,000,194 A | 3/1991 | van den Honert et al. |
| 5,135,001 A | 8/1992 | Sinofsky et al. |
| 5,374,285 A | 12/1994 | Vaiani et al. |
| 5,458,629 A | 10/1995 | Baudino et al. |
| 5,522,874 A | 6/1996 | Gates |
| 5,711,316 A | 1/1998 | Elsberry et al. |
| 5,713,922 A | 2/1998 | King |
| 5,800,350 A | 9/1998 | Coppleson et al. |
| 5,843,148 A | 12/1998 | Gijsbers et al. |
| 5,938,688 A | 8/1999 | Schiff |
| 5,987,361 A | 11/1999 | Mortimer |
| 6,018,684 A | 1/2000 | Bartig et al. |
| 6,134,478 A | 10/2000 | Spehr |
| 6,161,047 A | 12/2000 | King et al. |
| 6,167,311 A | 12/2000 | Rezai |
| 6,322,559 B1 | 11/2001 | Daulton et al. |
| 6,510,347 B2 | 1/2003 | Borkan |
| 6,556,873 B1 | 4/2003 | Smits |
| 6,564,078 B1 | 5/2003 | Marino et al. |
| 6,678,564 B2 | 1/2004 | Ketterl et al. |
| 6,757,970 B1 | 7/2004 | Kuzma et al. |
| 7,027,852 B2 | 4/2006 | Helland |
| 7,047,084 B2 | 5/2006 | Erickson et al. |
| 7,203,548 B2 | 4/2007 | Whitehurst et al. |
| 7,292,890 B2 | 11/2007 | Whitehurst et al. |
| 7,489,971 B1 | 2/2009 | Franz |
| 7,668,601 B2 | 2/2010 | Hegland et al. |
| 7,761,985 B2 | 7/2010 | Hegland et al. |
| 7,809,446 B2 | 10/2010 | Meadows |
| 7,822,482 B2 | 10/2010 | Gerber |
| 7,840,188 B2 | 11/2010 | Kurokawa |
| 7,848,802 B2 | 12/2010 | Goetz et al. |
| 7,856,707 B2 | 12/2010 | Cole |
| 7,860,570 B2 | 12/2010 | Whitehurst et al. |
| 7,974,705 B2 | 7/2011 | Zdeblick et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,099,177 B2 | 1/2012 | Dahlberg |
| 8,225,504 B2 | 7/2012 | Dye et al. |
| 8,295,944 B2 | 10/2012 | Howard et al. |
| 8,321,025 B2 | 11/2012 | Bedenbaugh |
| 8,359,107 B2 | 1/2013 | Pianca et al. |
| 8,391,985 B2 | 3/2013 | McDonald |
| 8,583,237 B2 | 11/2013 | Bedenbaugh |
| 8,649,873 B2 | 2/2014 | Moffitt et al. |
| 8,688,235 B1 | 4/2014 | Pianca et al. |
| 2001/0023368 A1 | 9/2001 | Black et al. |
| 2002/0156513 A1 | 10/2002 | Borkan |
| 2002/0183817 A1 | 12/2002 | Van Venrooij et al. |
| 2005/0015130 A1 | 1/2005 | Gill |
| 2005/0038489 A1 | 2/2005 | Grill |
| 2005/0171587 A1 | 8/2005 | Daglow et al. |
| 2006/0025841 A1 | 2/2006 | McIntyre |
| 2006/0247697 A1 | 11/2006 | Sharma et al. |
| 2007/0150036 A1 | 6/2007 | Anderson |
| 2007/0168007 A1 | 7/2007 | Kuzma et al. |
| 2007/0203546 A1 | 8/2007 | Stone et al. |
| 2007/0219551 A1 | 9/2007 | Honour et al. |
| 2008/0077186 A1 | 3/2008 | Thompson et al. |
| 2008/0103580 A1 | 5/2008 | Gerber |
| 2008/0114230 A1 | 5/2008 | Addis |
| 2008/0215125 A1 | 9/2008 | Farah et al. |
| 2008/0255647 A1 | 10/2008 | Jensen et al. |
| 2009/0187222 A1 | 7/2009 | Barker |
| 2009/0204192 A1 | 8/2009 | Carlton et al. |
| 2009/0276021 A1 | 11/2009 | Meadows |
| 2010/0030298 A1 | 2/2010 | Martens et al. |
| 2010/0036468 A1 | 2/2010 | Decre et al. |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0005069 A1 | 1/2011 | Pianca |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0238129 A1 | 9/2011 | Moffitt et al. |
| 2011/0245903 A1 | 10/2011 | Schulte et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2013/0109254 A1 | 5/2013 | Klardie et al. |
| 2013/0197424 A1 | 8/2013 | Bedenbaugh |
| 2013/0197602 A1 | 8/2013 | Pianca at al. |
| 2013/0261684 A1 | 10/2013 | Howard |
| 2013/0317587 A1 | 11/2013 | Barker |
| 2013/0325091 A1 | 12/2013 | Pianca et al. |
| 2014/0039587 A1 | 2/2014 | Romero |
| 2014/0039590 A1 | 2/2014 | Moffitt et al. |
| 2014/0123484 A1 | 5/2014 | DiGiore et al. |
| 2014/0142671 A1 | 5/2014 | Moffitt et al. |
| 2014/0155971 A1 | 6/2014 | Pianca et al. |
| 2014/0180375 A1 | 6/2014 | Pianca et al. |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 9732628 A1 | 9/1997 |
| WO | 9555411 A3 | 2/2000 |
| WO | 0038574 A1 | 7/2000 |
| WO | 0158520 A1 | 8/2001 |
| WO | 02068042 A1 | 9/2002 |
| WO | 2004045707 A1 | 6/2004 |
| WO | 2008018067 A2 | 2/2008 |
| WO | 2008053789 A1 | 5/2008 |
| WO | 2008/100841 A1 | 8/2008 |
| WO | 2009025816 A1 | 2/2009 |
| WO | 2009102536 A1 | 8/2009 |
| WO | 2013162775 A2 | 10/2013 |
| WO | 2014018092 A1 | 1/2014 |

OTHER PUBLICATIONS

U.S. Appl. No. 14/332,212, filed Jul. 15, 2014.
U.S. Appl. No. 14/452,461, filed Aug. 5, 2014.
U.S. Appl. No. 14/286,797, filed May 23, 2014.
U.S. Appl. No. 14/286,934, filed May 23, 2014.
International Search Report and Written Opinion for International Patent Application No. PCT/US2011/056582 mailed Feb. 22, 2012.
Official Communication for U.S. Appl. No. 13/275,112 mailed Mar. 10, 2014.
Official Communication for U.S. Appl. No. 13/275,112 mailed Sep. 16, 2013.
Official Communication for U.S. Appl. No. 13/275,112 mailed Oct. 15, 2012.
U.S. Appl. No. 14/469,214, filed Aug. 26, 2014.

METHODS FOR MAKING LEADS WITH SEGMENTED ELECTRODES FOR ELECTRICAL STIMULATION SYSTEMS

CROSS-REFERENCE TO RELATED APPLICATIONS

This application is a continuation of U.S. patent application Ser. No. 13/275,112 filed Oct. 17, 2011 which claims the benefit under 35 U.S.C. §119(e) of U.S. Provisional Patent Application Ser. No. 61/426,784 filed on Dec. 23, 2010, both of which are incorporated herein by reference.

FIELD

The invention is directed to the area of electrical stimulation systems and methods of making and using the systems. The present invention is also directed to electrical stimulation leads with multiple sets of segmented electrodes, as well as methods of making and using the segmented electrodes, leads, and electrical stimulation systems.

BACKGROUND

Electrical stimulation can be useful for treating a variety of conditions. Deep brain stimulation can be useful for treating, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. Typically, the electrodes are formed into rings disposed on a distal portion of the lead. The stimulus current projects from the ring electrodes equally in every direction. Because of the ring shape of these electrodes, the stimulus current cannot be directed to one or more specific positions around the ring electrode (e.g., on one or more sides, or points, around the lead). Consequently, undirected stimulation may result in unwanted stimulation of neighboring neural tissue, potentially resulting in undesired side effects.

BRIEF SUMMARY

One embodiment is a method of making a stimulation lead that includes providing a pre-electrode assembly comprising a plurality of segmented electrodes and a plurality of raised connectors. Each of the segmented electrodes is coupled to at least one other of the segmented electrodes by at least one of the raised connectors. The method further includes forming the pre-electrode assembly into a tube with the tube defining a longitudinal axis. Each of the raised connectors is disposed at a radius with respect to the longitudinal axis that is greater than a radius of any of the segmented electrodes with respect to the longitudinal axis. The method also includes forming at least a portion of a lead body around the segmented electrodes of the pre-electrode assembly; and grinding the tube comprising the pre-electrode assembly and portion of the lead body to remove the plurality of raised connectors leaving the plurality of segmented electrodes and the portion of the lead body.

Another embodiment is an assembly for forming a stimulation lead that includes a lead body having a distal end and a proximal end; and a pre-electrode assembly formed in a tube around a portion of the distal end of the lead body and comprising a plurality of segmented electrodes and a plurality of raised connectors. Each of the segmented electrodes is coupled to at least one other of the segmented electrodes by at least one of the raised connectors. The tube defines a longitudinal axis and each of the raised connectors is disposed at a radius with respect to the longitudinal axis that is greater than a radius of any of the segmented electrodes with respect to the longitudinal axis.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The invention is directed to the area of electrical stimulation systems and methods of making and using the systems.

The present invention is also directed to forming electrical stimulation leads with multiple sets of segmented electrodes, as well as methods of making and using the segmented electrodes, leads, and electrical stimulation systems.

A lead for deep brain stimulation may include stimulation electrodes, recording electrodes, or a combination of both. At least some of the stimulation electrodes, recording electrodes, or both are provided in the form of segmented electrodes that extend only partially around the circumference of the lead. These segmented electrodes can be provided in sets of electrodes, with each set having electrodes radially distributed about the lead at a particular longitudinal position.

A practitioner may determine the position of the target neurons using the recording electrode(s) and then position the stimulation electrode(s) accordingly without removal of a recording lead and insertion of a stimulation lead. In some embodiments, the same electrodes can be used for both recording and stimulation. In some embodiments, separate leads can be used; one with recording electrodes which identify target neurons, and a second lead with stimulation electrodes that replaces the first after target neuron identification. A lead may include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes. For illustrative purposes, the leads are described herein relative to use for deep brain stimulation, but it will be understood that any of the leads can be used for applications other than deep brain stimulation.

Deep brain stimulation devices and leads are described in, for example, U.S. Pat. No. 7,809,446 ("Devices and Methods For Brain Stimulation"), U.S. Patent Application Publication No. 2010/0076535 A1 ("Leads With Non-Circular-Shaped Distal Ends For Brain Stimulation Systems and Methods of Making and Using"), U.S. Patent Application Publication 2007/0150036 A1 ("Stimulator Leads and Methods For Lead Fabrication"), U.S. patent application Ser. No. 12/177,823 ("Lead With Transition and Methods of Manufacture and Use"), U.S. Patent Application Publication No. 2009/0276021 A1 ("Electrodes For Stimulation Leads and Methods of Manufacture and Use"), U.S. Patent Application Ser. No. 61/170,037 ("Deep Brain Stimulation Current Steering with Split Electrodes"), U.S. Patent Application Ser. No. 61/022,953, U.S. Patent Application Ser. No. 61/316,759, and U.S. Patent Application Publication No. 2009/0187222 A1. Each of these references is incorporated herein by reference.

Figure 1:
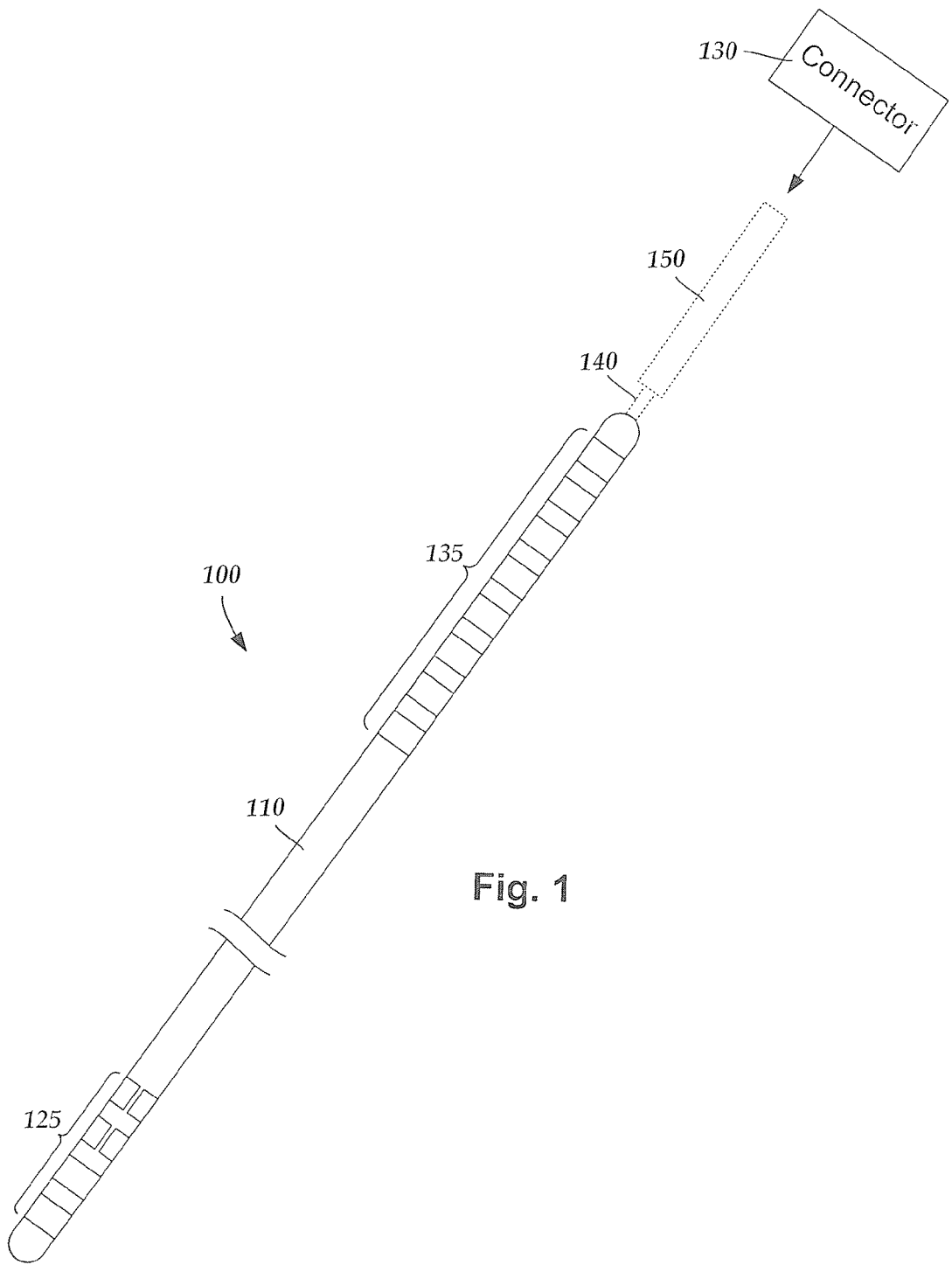
FIG. 1 is a schematic side view of one embodiment of a device for brain stimulation, according to the invention.

FIG. 1 illustrates one embodiment of a device 100 for brain stimulation. The device includes a lead 110, a plurality of electrodes 125 disposed at least partially about a circumference of the lead 110, a plurality of terminals 135, a connector 130 for connection of the electrodes to a control unit, and a stylet 140 for assisting in insertion and positioning of the lead in the patient's brain. The stylet 140 can be made of a rigid material. Examples of suitable materials for the stylet include, but are not limited to, tungsten, stainless steel, and plastic. The stylet 140 may have a handle 150 to assist insertion into the lead 110, as well as rotation of the stylet 140 and lead 110. The connector 130 fits over a proximal end of the lead 110, preferably after removal of the stylet 140.

The control unit (not shown) is typically an implantable pulse generator that can be implanted into a patient's body, for example, below the patient's clavicle area. The pulse generator can have eight stimulation channels which may be independently programmable to control the magnitude of the current stimulus from each channel. In some cases the pulse generator may have more than eight stimulation channels (e.g., 16-, 32-, or more stimulation channels). The control unit may have one, two, three, four, or more connector ports, for receiving the plurality of terminals 135 at the proximal end of the lead 110.

In one example of operation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of the stylet 140. The lead 110 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the circumference of the lead 110 to stimulate the target neurons. Stimulation electrodes may be ring-shaped so that current projects from each electrode equally in every direction from the position of the electrode along a length of the lead 110. Ring electrodes, however, typically do not enable stimulus current to be directed to only one side of the lead. Segmented electrodes, however, can be used to direct stimulus current to one side, or even a portion of one side, of the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead).

To achieve current steering, segmented electrodes can be utilized in addition to, or as an alternative to, ring electrodes. Though the following description discusses stimulation electrodes, will be understood that all configurations of the stimulation electrodes discussed may be utilized in arranging recording electrodes as well.

Figure 2:
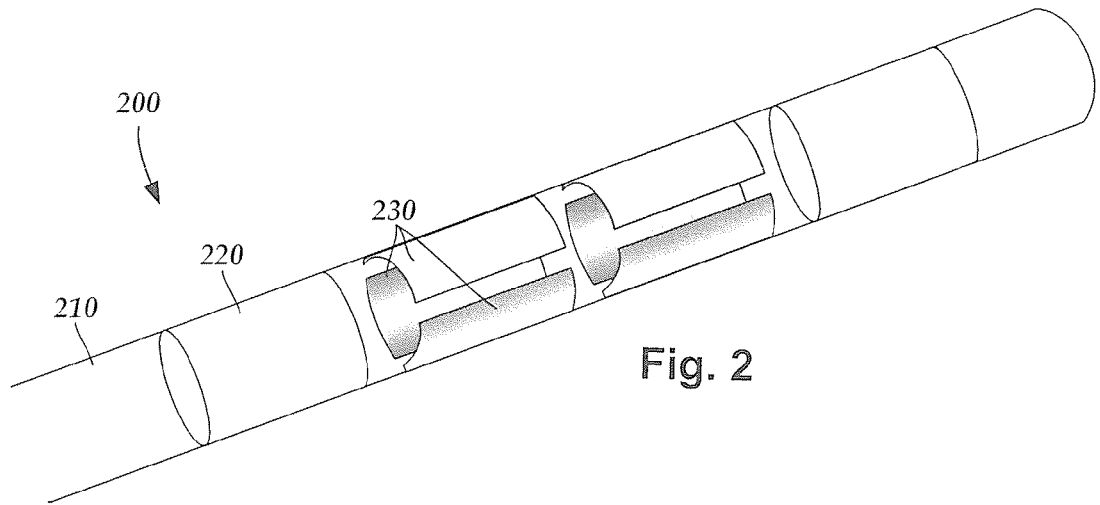
FIG. 2 is a schematic perspective view of one embodiment of a portion of a lead having a plurality of segmented electrodes, according to the invention.

FIG. 2 illustrates one embodiment of a distal portion of a lead 200 for brain stimulation. The lead 200 includes a lead body 210, one or more optional ring electrodes 220, and a plurality of sets of segmented electrodes 230. The lead body 210 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 200 may be in contact with body tissue for extended periods of time. In at least some embodiments, the lead 200 has a cross-sectional diameter of no more than 1.5 mm and may be in the range of 1 to 1.5 mm. In at least some embodiments, the lead 200 has a length of at least 10 cm and the length of the lead 200 may be in the range of 25 to 70 cm.

The electrodes may be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Stimulation electrodes in the form of ring electrodes 220 may be disposed on any part of the lead body 210, usually near a distal end of the lead 200. In FIG. 2, the lead 200 includes two ring electrodes 220. Any number of ring electrodes 220 may be disposed along the length of the lead body 210 including, for example, one, two three, four, five, six, seven, eight, nine, ten, eleven, twelve, thirteen, fourteen, fifteen, sixteen or more ring electrodes 220. It will be understood that any number of ring electrodes may be disposed along the length of the lead body 210. In some embodiments, the ring electrodes 220 are substantially cylindrical and wrap around the entire circumference of the lead body 210. In some embodiments, the outer diameters of the ring electrodes 220 are substantially equal to the outer diameter of the lead body 210. The length of the ring electrodes 220 may vary according to the desired treatment and the location of the target neurons. In some embodiments the length of the ring electrodes 220 are less than or equal to the diameters of the ring electrodes 220. In other embodiments, the lengths of the ring electrodes 220 are greater than the diameters of the ring electrodes 220.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue.

In FIG. 2, the lead 200 is shown having a plurality of segmented electrodes 230. Any number of segmented electrodes 230 may be disposed on the lead body 210 including, for example, one, two three, four, five, six, seven, eight, nine, ten, eleven, twelve, thirteen, fourteen, fifteen, sixteen or more segmented electrodes 230. It will be understood that any number of segmented electrodes 230 may be disposed along the length of the lead body 210.

The segmented electrodes 230 may be grouped into sets of segmented electrodes, where each set is disposed around a circumference of the lead 200 at a particular longitudinal portion of the lead 200. The lead 200 may have any number segmented electrodes 230 in a given set of segmented electrodes. The lead 200 may have one, two, three, four, five, six, seven, eight, or more segmented electrodes 230 in a given set. In at least some embodiments, each set of segmented electrodes 230 of the lead 200 contains the same number of segmented electrodes 230. The segmented electrodes 230 disposed on the lead 200 may include a different number of electrodes than at least one other set of segmented electrodes 230 disposed on the lead 200.

The segmented electrodes 230 may vary in size and shape. In some embodiments, the segmented electrodes 230 are all of the same size, shape, diameter, width or area or any combination thereof. In some embodiments, the segmented electrodes 230 of each circumferential set (or even all segmented electrodes disposed on the lead 200) may be identical in size and shape.

Each set of segmented electrodes 230 may be disposed around the circumference of the lead body 210 to form a substantially cylindrical shape around the lead body 210. The spacing between individual electrodes of a given set of the segmented electrodes may be the same, or different from, the spacing between individual electrodes of another set of segmented electrodes on the lead 200. In at least some embodiments, equal spaces, gaps or cutouts are disposed between each segmented electrode 230 around the circumference of the lead body 210. In other embodiments, the spaces, gaps or cutouts between the segmented electrodes 230 may differ in size or shape. In other embodiments, the spaces, gaps, or cutouts between segmented electrodes 230 may be uniform for a particular set of the segmented electrodes 230, or for all sets of the segmented electrodes 230. The sets of segmented electrodes 230 may be positioned in irregular or regular intervals along a length the lead body 210.

Conductor wires that attach to the ring electrodes 220 or segmented electrodes 230 extend along the lead body 210. These conductor wires may extend through the material of the lead 20 or along one or more lumens defined by the lead 200, or both. The conductor wires are presented at a connector (via terminals) for coupling of the electrodes 220, 230 to a control unit (not shown).

Figure 3A:
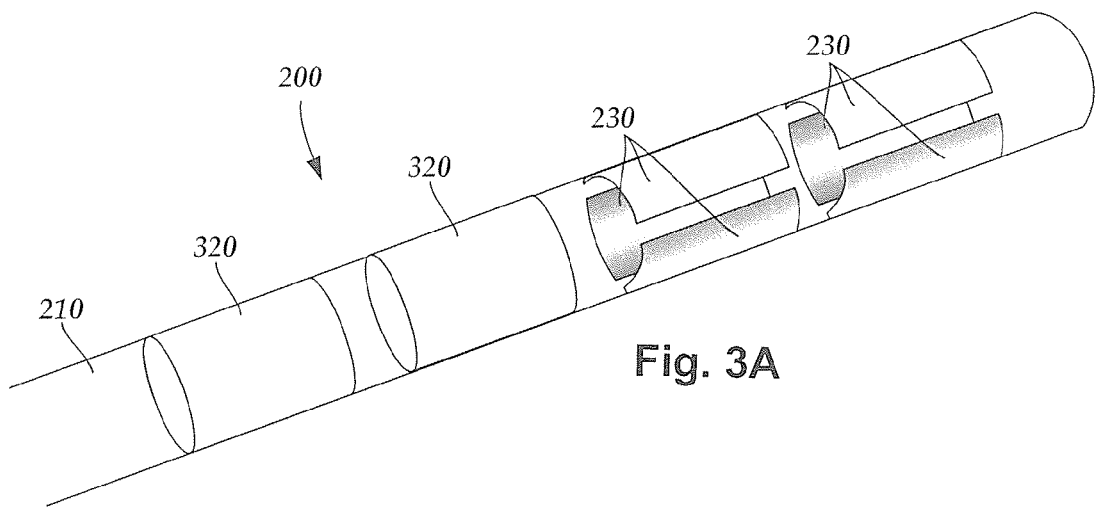
FIG. 3A is a perspective view of a third embodiment of a portion of a lead having a plurality of segmented electrodes, according to the invention.
Figure 3B:
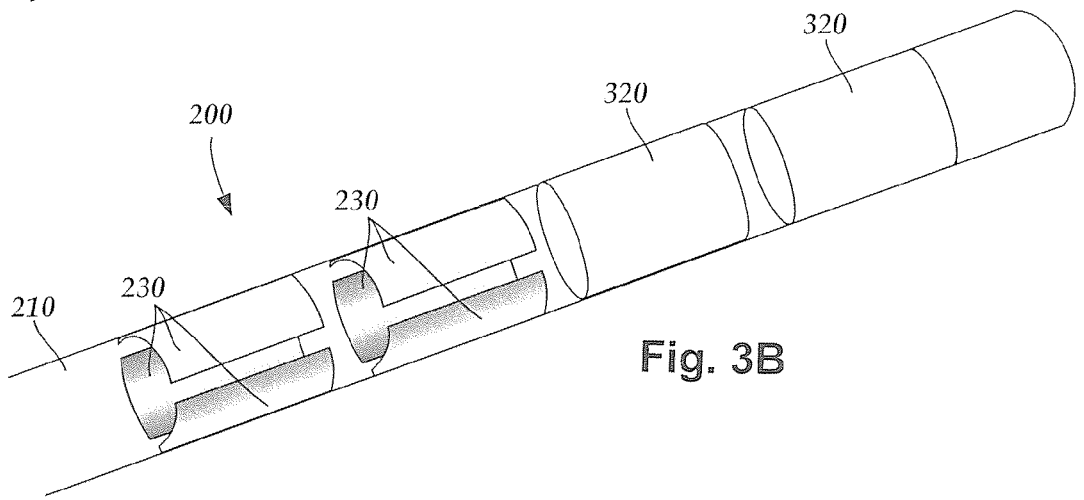
FIG. 3B is a perspective view of a fourth embodiment of a portion of a lead having a plurality of segmented electrodes, according to the invention.

When the lead 200 includes both ring electrodes 220 and segmented electrodes 230, the ring electrodes 220 and the segmented electrodes 230 may be arranged in any suitable configuration. For example, when the lead 200 includes two sets of ring electrodes 220 and two sets of segmented electrodes 230, the ring electrodes 220 can flank the two sets of segmented electrodes 230 (see e.g., FIG. 2). Alternately, the two sets of ring electrodes 220 can be disposed proximal to the two sets of segmented electrodes 230 (see e.g., FIG. 3A), or the two sets of ring electrodes 220 can be disposed distal to the two sets of segmented electrodes 230 (see e.g., FIG. 3B). It will be understood that other configurations are possible as well (e.g., alternating ring and segmented electrodes, or the like).

By varying the location of the segmented electrodes 230, different coverage of the target neurons may be selected. For example, the electrode arrangement of FIG. 3A may be useful if the physician anticipates that the neural target will be closer to a distal tip of the lead body 210, while the electrode arrangement of FIG. 3B may be useful if the physician anticipates that the neural target will be closer to a proximal end of the lead body 210.

Any combination of ring electrodes 220 and segmented electrodes 230 may be disposed on the lead 200. For example, the lead may include a first ring electrode 120, two sets of segmented electrodes, each set formed of three segmented electrodes 230, and a final ring electrode 120 at the end of the lead. This configuration may simply be referred to as a 1-3-3-1 configuration. It may be useful to refer to the electrodes with this shorthand notation. Thus, the embodiment of FIG. 3A may be referred to as a 1-1-3-3 configuration, while the embodiment of FIG. 3B may be referred to as a 3-3-1-1 configuration. Other eight-electrode configurations include, for example, a 2-2-2-2 configuration, where four sets of segmented electrodes are disposed on the lead, and a 4-4 configuration, where two sets of segmented electrodes, each having four segmented electrodes 230 are disposed on the lead. In some embodiments, the lead includes 16 electrodes. Possible configurations for a 16-electrode lead include, but are not limited to 4-4-4-4; 8-8; 3-3-3-3-3-1 (and all rearrangements of this configuration); and 2-2-2-2-2-2-2-2.

Figure 4:
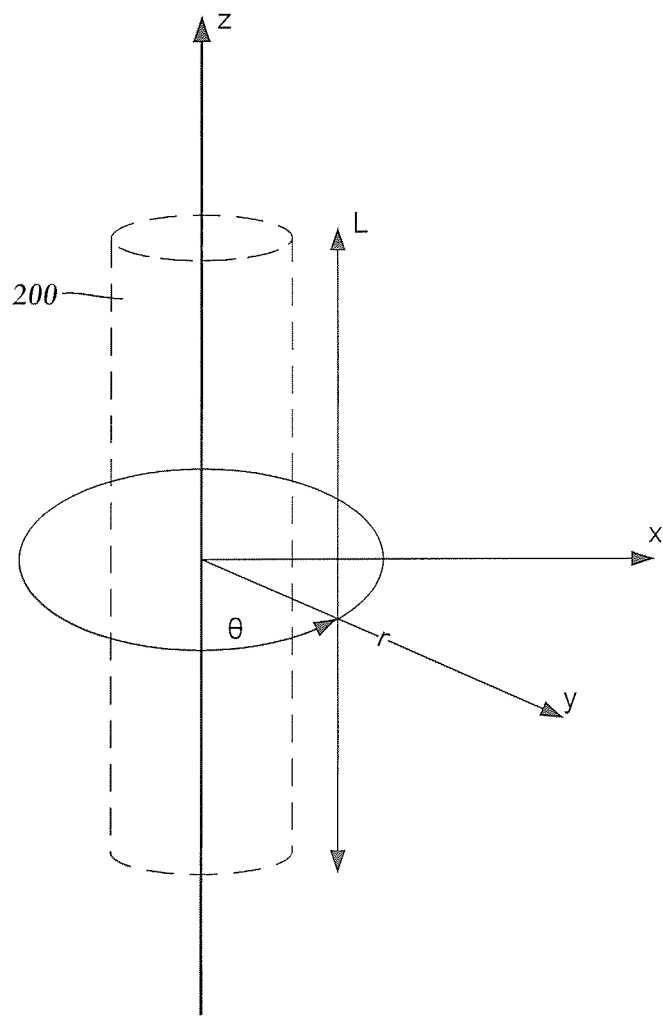
FIG. 4 is a schematic diagram of radial current steering along various electrode levels along the length of a lead, according to the invention.

FIG. 4 is a schematic diagram to illustrate radial current steering along various electrode levels along the length of the lead 200. While conventional lead configurations with ring electrodes are only able to steer current along the length of the lead (the z-axis), the segmented electrode configuration is capable of steering current in the x-axis, y-axis as well as the z-axis. Thus, the centroid of stimulation may be steered in any direction in the three-dimensional space surrounding the lead 200. In some embodiments, the radial distance, r, and the angle θ around the circumference of the lead 200 may be dictated by the percentage of anodic current (recognizing that stimulation predominantly occurs near the cathode, although strong anodes may cause stimulation as well) introduced to each electrode. In at least some embodiments, the configuration of anodes and cathodes along the segmented electrodes allows the centroid of stimulation to be shifted to a variety of different locations along the lead 200.

As can be appreciated from FIG. 4, the centroid of stimulation can be shifted at each level along the length of the lead 200. The use of multiple sets of segmented electrodes at different levels along the length of the lead allows for three-dimensional current steering. In some embodiments, the sets of segmented electrodes are shifted collectively (i.e., the centroid of simulation is similar at each level along the length of the lead). In at least some other embodiments, each set of segmented electrodes is controlled independently. Each set of segmented electrodes may contain two, three, four, five, six, seven, eight or more segmented electrodes. It will be understood that different stimulation profiles may be produced by varying the number of segmented electrodes at each level.

For example, when each set of segmented electrodes includes only two segmented electrodes, uniformly distributed gaps (inability to stimulate selectively) may be formed in the stimulation profile. In some embodiments, at least three segmented electrodes 230 in a set are utilized to allow for true 360° selectivity.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The reliability and durability of the lead will depend heavily on the design and method of manufacture. Fabrication techniques discussed below provide methods that can produce manufacturable and reliable leads.

When the lead 200 includes a plurality of sets of segmented electrodes 230, it may be desirable to form the lead 200 such that corresponding electrodes of different sets of segmented electrodes 230 are radially aligned with one another along the length of the lead 200 (see e.g., the segmented electrodes 230 shown in FIG. 2). Radial alignment between corresponding electrodes of different sets of segmented electrodes 230 along the length of the lead 200 may reduce uncertainty as to the location or orientation between corresponding segmented electrodes of different sets of segmented electrodes. Accordingly, it may be beneficial to form electrode arrays such that corresponding electrodes of different sets of segmented electrodes along the length of the lead 200 are radially aligned with one another and do not radially shift in relation to one another during manufacturing of the lead 200.

Figure 5:
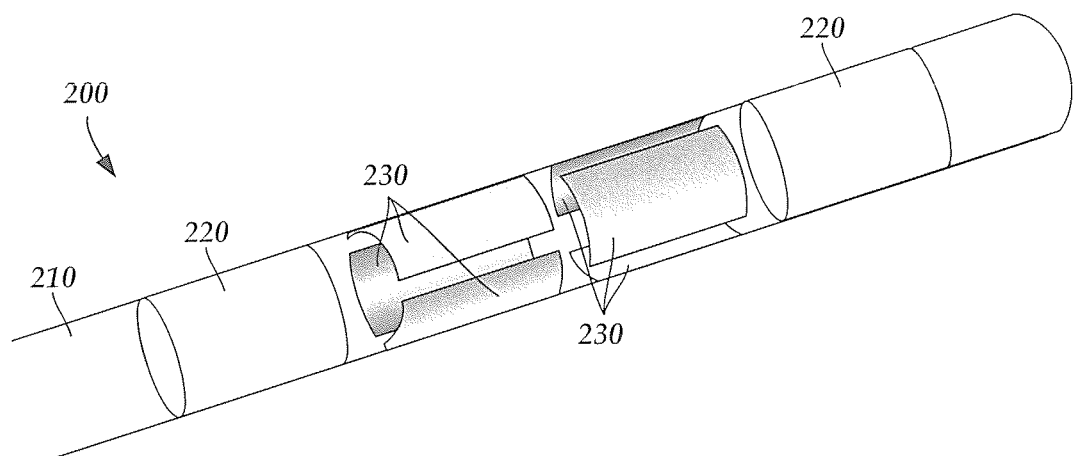
FIG. 5 is a perspective view of another embodiment of a portion of a lead having a plurality of segmented electrodes arranged in a staggered orientation, according to the invention.

FIG. 5 is a side view of another embodiment of the lead 200 having a plurality of sets of segmented electrodes. As shown in FIG. 5, individual electrodes in the two sets of segmented electrodes 230 are staggered relative to one another along the length of the lead body 210. In some cases, the staggered positioning of corresponding electrodes of different sets of segmented electrodes along the length of the lead 200 may be designed for a specific application.

Challenges to manufacturing leads with segmented electrodes include obtaining and maintaining the desired alignment of electrodes within a set of electrodes and between the set of electrodes. There may be challenges to maintaining a desired radial separation between electrodes of a set and axial separation between electrodes of different sets. In addition, there may be challenges to avoiding dislodgement of an electrode from the lead body.

Figure 6:
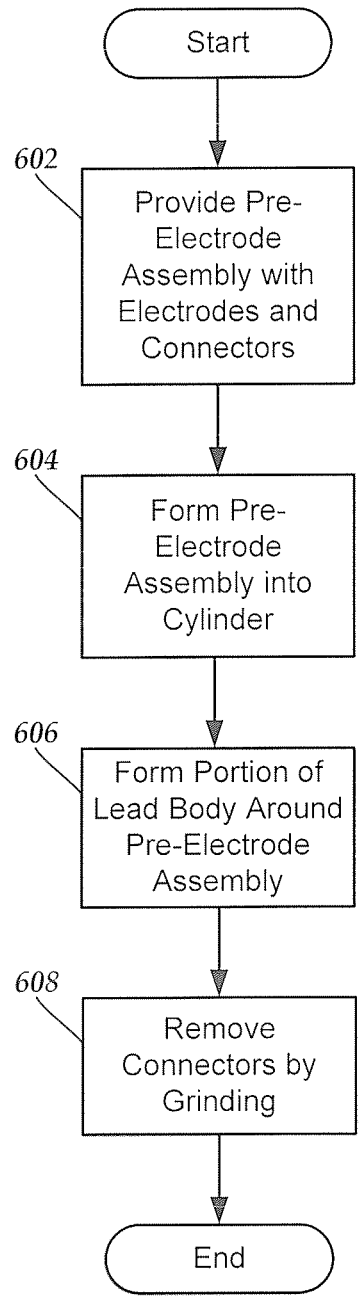
FIG. 6 is a flowchart of one embodiment of a method of making a lead, according to the invention.

A lead with segmented electrodes can be made in variety of different ways that can address (e.g., eliminate or reduce) these challenges. FIG. 6 is a flow diagram of a portion of one embodiment of a method of making a lead with segmented electrodes. In a first step 602, a pre-electrode assembly with electrodes and raised connectors is provided. Preferably, the pre-electrode assembly is a metal assembly with metal electrodes and metal connectors that couple the electrodes to each other. Preferably, the electrodes and connectors are formed from a single sheet of metal.

Figure 7A:
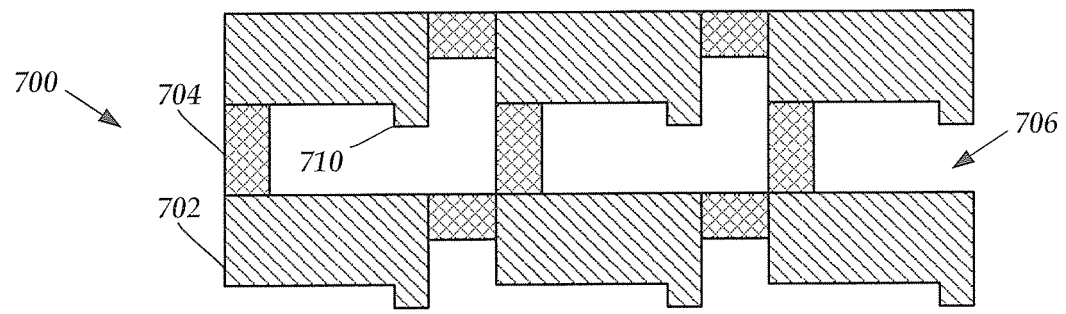
FIG. 7A is a schematic top plan view of one embodiment of a pre-electrode assembly, according to the invention.
Figure 7B:
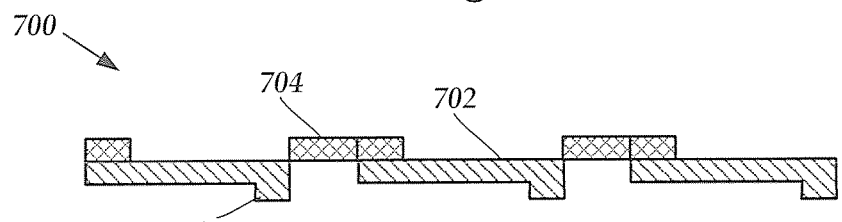
FIG. 7B is a schematic side plan view of the pre-electrode assembly of FIG. 7A, according to the invention.

FIGS. 7A and 7B illustrate one embodiment of a pre-electrode assembly 700 with electrodes 702 and raised connectors 704. Each electrode 702 is directly coupled to at least one other electrode by at least one, two, or three of the raised connectors 704. In at least some embodiments, the electrodes 702 are provided in a set of rows, in a set of columns, or in both rows and columns. The electrodes in a given row or column can be aligned with, or staggered with respect to, electrodes in an adjacent row or column. Typically, the electrodes in each row or column are directly coupled to the electrodes in an adjacent row or column using at least one, two, or three connectors. In some embodiments, each electrode in a row or column is directly coupled by a connector to an electrode in an adjacent row or column. In at least some embodiments, the electrodes are arranged in rows and columns and each electrode is directly coupled by a connector to an electrode in an adjacent column and directly coupled by a connector to an electrode in an adjacent row, as illustrated, for example, in FIG. 7A. In at least some embodiments, the electrodes are arranged in rows and columns and each electrode is directly coupled by at least one connector to an electrode in each adjacent column and directly coupled by at least one connector to an electrode in each adjacent row, as illustrated, for example, in FIG. 7A Although FIGS. 7A and 7B illustrate electrodes coupled to other electrodes using a single connector between two electrodes, it will be understood that multiple connectors can be used between two electrodes.

The raised connectors 704 are provided to hold the electrodes 702 in alignment during the manufacture of the lead and will be removed during manufacture as described below. Preferably, the electrodes 702 and connectors 704 are made of the same material. In at least some embodiments, the electrodes 702 and connectors 704 are formed from a single sheet of metal. Preferably, the pre-electrode assembly includes gaps 706 between the electrodes 702 and connectors 704. Preferably, the connectors 704 are raised above the electrodes 702 by an amount greater than a thickness of the connectors 704 and may be raised at least twice, three times, four times, or ten times the thickness of the connectors 704. This can facilitate removal of the connectors later in the process of manufacturing.

The connectors 704 can be any suitable size, width, length, and thickness. The length of the connectors 704 is the separation distance between the two electrodes coupled by the connector. The width and thickness can be selected to provide a desired amount of stability when maintaining the electrodes in the desired arrangement. It will be recognized that this factor is counterbalanced by the additional effort in forming a tube (see below) with a pre-electrode assembly with wider or thicker connectors; as well as the additional amount of material that will be removed with removal of the connectors. In some embodiments, the width of the connector is no more than half, one-third, or one-quarter of the length of the connector. It will be recognized that the width and thickness of each of the connectors can be uniform or can vary along the length of the connectors. It will also be recognized that the connectors may have the same lengths, widths, and thicknesses or there may be variation in these parameters between connectors.

The pre-electrode assembly 700 with electrodes 702 and connectors 704 can be formed by any suitable method. For example, the pre-electrode assembly 700 can be formed by stamping a sheet of metal or other conductive material or by machining or molding metal or other conductive material into the desired shape. Preferably, the stamping or molding of the pre-electrode assembly 700 results in the connectors 704 being raised with respect to the electrodes, as illustrated in FIGS. 7A and 7B. If not, the connectors 704 can be raised in a separate step by, for example, stamping (e.g., a second stamping step) or otherwise bending the pre-electrode assembly to form the raised connectors. The gaps 706 between electrodes and between connectors may be formed when the pre-electrode assembly is formed by stamping or molding. Alternatively or additionally, some or all of the gaps may be formed prior to stamping or after stamping or molding; for example, the gaps may be formed by stamping, cutting, and the like.

Optionally, the electrodes 702 can include tabs 710. The tabs may be folded down during manufacture to interlock the electrodes with the material of the lead body described below. The tabs can protrude into the lead body and provide an anchoring mechanism to prevent dislodgment of the individual electrode segments.

Figure 8:
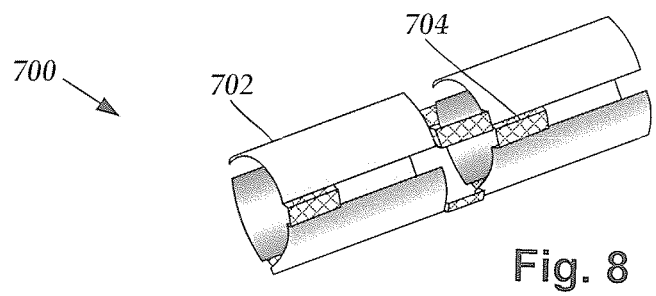
FIG. 8 is a schematic perspective view of one embodiment of a pre-electrode assembly wrapped into a tube, according to the invention.
Figure 9:
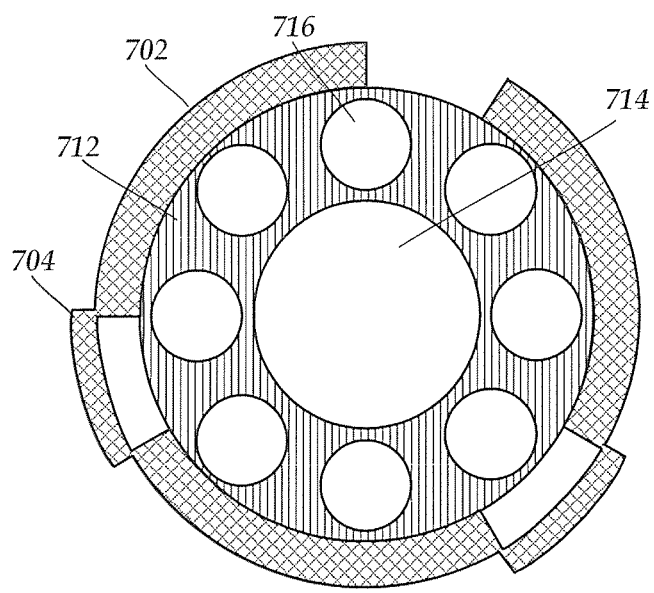
FIG. 9 is a cross-sectional view of one embodiment of a pre-electrode assembly wrapped around a lead tube, according to the invention.

Returning to FIG. 6, in step 604, the pre-electrode assembly is formed into a tube, as illustrated, for example, in FIG. 8. In at least some embodiments, the pre-electrode assembly 700 is wrapped around a mandrel or other cylindrical element to facilitate formation of the tube. In one embodiment the pre-electrode assembly 700 is wrapped around a lead tube 712 that includes a central lumen 714 and optionally one or more conductor lumens 716 as illustrated, for example, in FIG. 9. Although the embodiments illustrated in FIGS. 8 and 9 show a tube with a circular cross-section, it will be understood that other types of tubes can be formed including, but not limited to, tubes with square, rectangular, oval, triangular, hexagonal, or octagonal cross-sections. In another embodiment, the pre-electrode assembly can be formed or rolled into a cylinder.

The tube formed by the pre-electrode assembly defines a longitudinal axis along the tube. Preferably, each of the raised connectors is disposed at a radius with respect to the longitudinal axis that is greater than a radius of any of the electrodes.

The pre-electrode assembly can be held in the cylindrical form by any suitable method. For example, straps or fasteners may be attached to the pre-electrode assembly, or wrapped around the pre-electrode assembly, to hold it in the cylindrical form. Alternatively or additionally, two or more portions of the pre-electrode assembly may overlap and the overlapping regions of the carrier can be attached to each other by welding, soldering, application of adhesive, or the like. In other embodiments, the forming process will cause the metal to yield and hence the material will take a permanent change in shape by, for example, deformation of the material.

In at least some embodiments, conductor wires (not shown) are attached to the individual electrodes 402 before or after forming the pre-electrode assembly into a tube. The conductor wires can be, for example, insulated wires with a portion of the insulation removed to make contact with the electrodes 702. A different conductor wire can be attached to each electrode 702. In other embodiments, the same conductor wire may be attached to two or more of the electrodes.

The conductor wires can be attached by any suitable method including, but not limited to, welding, soldering, crimping, staking, using a conductive adhesive, and the like. The conductor wires can be attached to any suitable part of the electrodes 702. In some embodiments, the conductor wires are disposed in conductor lumens 716 (see, e.g., FIG. 9). One or more conductor wires may be disposed in each conductor lumen. In at least some embodiments, each conductor lumen has a single conductor wire disposed therein. Portions of the conductor lumens can be exposed (e.g., by ablating or removing a portion of the lead tube) to provide access for attachment of the conductor wire to the electrode.

Figure 10:
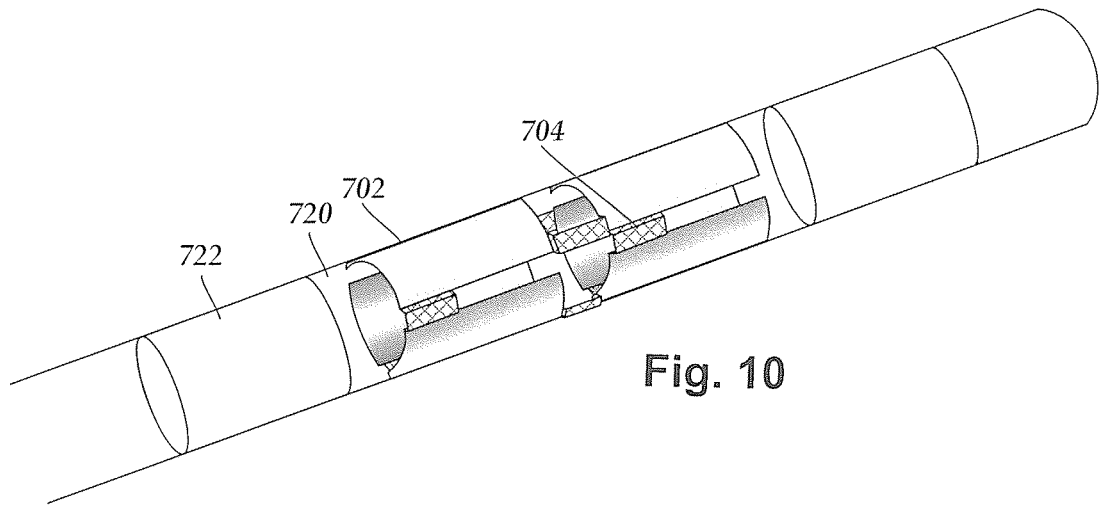
FIG. 10 is a schematic perspective view of the pre-electrode assembly of FIG. 8 with a portion of the lead body formed around it, according to the invention.
Figure 11:
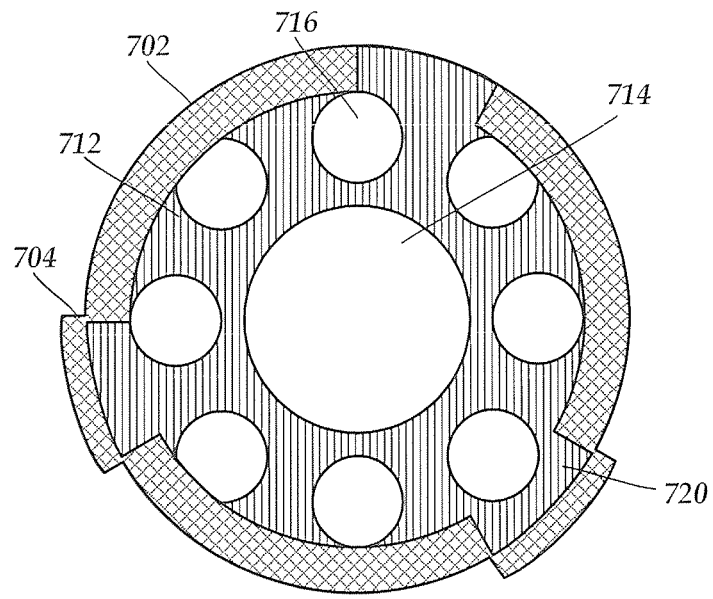
FIG. 11 is a cross-sectional view of one embodiment of a pre-electrode assembly with a portion of the lead body formed around it, according to the invention.

Returning to FIG. 6, in step 606 at least a portion of the lead body is formed around the pre-electrode assembly. FIG. 10 illustrates one embodiment of the pre-electrode assembly 700 with a portion 720 of the lead body formed around the electrodes 702 and connectors 704 of the pre-electrode assembly. FIG. 11 is a cross-sectional view illustrating the electrodes 702 and connectors 704 with a portion 720 of the lead body. As illustrated in FIG. 11, preferably a portion of the lead body 720 is formed beneath the connectors 704. Preferably, the portion of the lead body that is formed is capable of retaining the electrodes 702 within the lead and in the desired orientation and configuration after removal of the connectors, as described below. Optionally, the formation of the lead body may also incorporate other electrodes, such as ring electrodes 722, into the structure of the lead. In some embodiments, the portion of the lead body may incorporate pre-existing structures, such as the lead tube 712 of FIG. 9, into the lead body during its formation as illustrated, for example, in FIG. 11.

The portion of the lead body can be formed by any suitable method including, but not limited to, molding the portion of the lead body around the pre-electrode assembly. As another example, polymeric material, such as polymer tubing polyurethane or silicone tubing), may be placed over the pre-electrode assembly and then heated to allow the material of the polymer tubing to reflow and form the portion of the lead body. In some embodiments, a heat shrink tube may be temporarily placed over the polymer tubing, prior to reflow, so that the material of the polymer tubing is retained during reflow. The heat shrink tubing may then be removed (e.g., cut off) after reflow of the polymer tubing.

Figure 12:
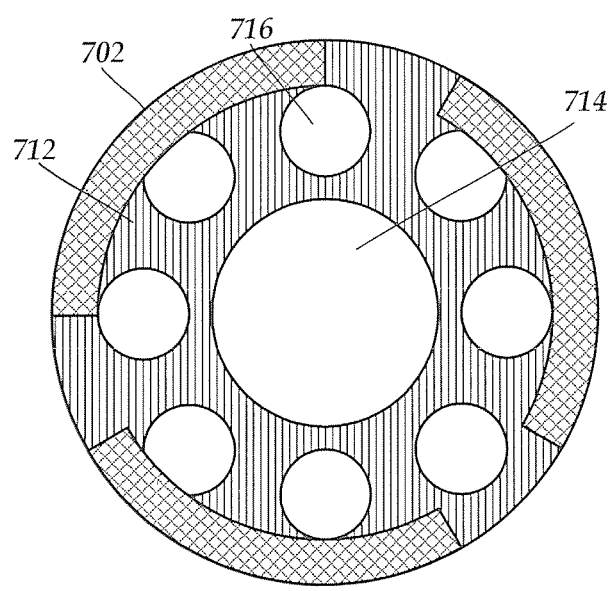
FIG. 12 is a cross-sectional view of one embodiment of a lead with the raised connectors of the pre-electrode assembly removed, according to the invention.

Returning to FIG. 6, in step 608 the connectors are removed by grinding. FIGS. 2 and 12 illustrate embodiments of a lead after removal of the connectors. In some embodiments, the connectors are removed by centerless grinding. Optionally, the grinding may also remove portions of the lead body, the electrodes, or both. In at least some embodiments, the grinding provides a lead that is isodiametric at the distal end or along the entire lead.

The above specification, examples, and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An assembly for forming a stimulation lead, comprising:
   a lead body having a distal end and a proximal end; and
   a pre-electrode assembly formed in a tube around a portion of the distal end of the lead body and comprising a plurality of segmented electrodes and a plurality of connectors, wherein each of the segmented electrodes is coupled to at least one other of the segmented electrodes by at least one of the connectors and the segmented electrodes and the connectors are formed of conductive material, the tube defining a longitudinal axis, wherein each of the connectors is disposed so that an outer radius of the connector with respect to the longitudinal axis is greater than an outer radius of any of the segmented electrodes with respect to the longitudinal axis.

2. The assembly of claim 1, wherein the segmented electrodes and the connectors are formed of a same conductive material.

3. The assembly of claim 1, wherein a portion of each of the connectors circumferentially overlaps a portion of at least one of the segmented electrodes.

4. The assembly of claim 1, further comprising at least one ring electrode disposed around a portion of the distal end of the lead body.

5. The assembly of claim 1, wherein the segmented electrodes are arranged in rows with each row at a same longitudinal position on the tube, wherein each of the segmented electrodes is directly coupled by at least one of the connectors to at least one other of the segmented electrodes in a same row.

6. The assembly of claim 1, wherein the segmented electrodes are arranged in rows with each row at a same longitudinal position on the tube, wherein each of the segmented electrodes is directly coupled by at least one of the connectors to at least two other of the segmented electrodes in a same row.

7. The assembly of claim 1, wherein the segmented electrodes are arranged in rows and columns and wherein each segmented electrode is directly coupled to a segmented electrode of an adjacent row using a one of the plurality of connectors and directly coupled to a segmented electrode of an adjacent column using another one of the plurality of connectors.

8. The assembly of claim 1, further comprising a tab extending from at least one of the segmented electrodes into the lead body.

9. The assembly of claim 1, wherein the plurality of segmented electrodes comprises a first segmented electrode and a second segmented electrode, wherein the first segmented electrode and the second segmented electrode are disposed circumferentially around the tube at a same longitudinal position along the tube, wherein at least one of the connectors directly couples to both the first segmented electrode and the second segmented electrode.

10. A method of making a stimulation lead, the method comprising:
    providing the assembly of claim 1; and
    grinding the assembly to remove the plurality of connectors leaving the plurality of segmented electrodes and at least a portion of the lead body.

11. The method of claim 10, wherein providing the assembly comprises stamping a metal sheet to form the plurality of segmented electrodes and the plurality of connectors.

12. The method of claim 10, wherein each of the connectors has an inner radius and an inner radius of each of the connectors of the assembly prior to grinding is greater than an outer radius of each of the segmented electrodes after grinding.

13. The method of claim 10, wherein a portion of each of the connectors circumferentially overlaps a portion of at least one of the segmented electrodes.

14. The method of claim 10, wherein providing the assembly comprises forming a tab extending from at least one of the plurality of segmented electrodes.

15. The method of claim 10, wherein the plurality of segmented electrodes comprises a first segmented electrode and a second segmented electrode, wherein the first segmented electrode and the second segmented electrode are disposed circumferentially around the tube at a same longitudinal position along the tube, wherein at least one of the connectors is directly coupled to both the first segmented electrode and the second segmented electrode.

16. The method of claim 10, wherein the segmented electrodes and the connectors are formed of a same conductive material.

17. The method of claim 10, further comprising attaching a conductor wire to at least one of the segmented electrodes.

18. The method of claim 10, wherein providing the assembly comprises molding the lead body around the segmented electrodes.

19. The method of claim 18, wherein molding the lead body comprises disposing a polymeric tubing around the assembly; disposing a heat-shrink tubing over the polymeric tubing; heating the polymeric tubing to reflow the polymeric tubing around the segmented electrodes; and removing the heat-shrink tubing.

20. The method of claim 10, wherein grinding the tube comprises grinding the tube to form an isodiametric lead.

* * * * *